US009055875B2

(12) United States Patent
Triantis et al.

(10) Patent No.: US 9,055,875 B2
(45) Date of Patent: Jun. 16, 2015

(54) METHOD AND APPARATUS FOR MEASURING ACTIVITY IN THE PERIPHERAL NERVOUS SYSTEM

(75) Inventors: Iasonas Triantis, London (GB); Christofer Toumazou, London (GB)

(73) Assignee: VAGONYX LIMITED, Tortola (VG)

(*) Notice: Subject to any disclaimer, the term of this patent is extended or adjusted under 35 U.S.C. 154(b) by 1368 days.

(21) Appl. No.: 12/373,491

(22) PCT Filed: Jul. 5, 2007

(86) PCT No.: PCT/GB2007/002552
§ 371 (c)(1),
(2), (4) Date: Apr. 17, 2009

(87) PCT Pub. No.: WO2008/007065
PCT Pub. Date: Jan. 17, 2008

(65) Prior Publication Data
US 2009/0292345 A1  Nov. 26, 2009

(30) Foreign Application Priority Data

Jul. 10, 2006 (GB) .................. 0613698.0

(51) Int. Cl.
*A61B 5/04* (2006.01)
*A61B 5/00* (2006.01)
(52) U.S. Cl.
CPC ........... *A61B 5/04001* (2013.01); *A61B 5/7217* (2013.01)
(58) Field of Classification Search
CPC ..................... A61B 5/04001; A61B 5/7217
See application file for complete search history.

(56) References Cited

U.S. PATENT DOCUMENTS

| 5,487,756 A * | 1/1996 | Kallesoe et al. ............. 607/118 |
| 2003/0236558 A1 | 12/2003 | Whitehurst et al. |
| 2004/0015204 A1* | 1/2004 | Whitehurst et al. ............. 607/48 |

FOREIGN PATENT DOCUMENTS

WO    2005067792 A1    4/2005

OTHER PUBLICATIONS

Bermejo (Mira and Alverez, Artificial Neural Nets 2003, Springer:297-298).*
Poghossian et al. (Electroanalysis 2004, 16(22):1863-1872).*
Neurotransmitter Review (Alcohol Health & Research World. 1997, vol. 21 (2); pp. 107-108).*
The Neuron: Cell and Molecular Biology (2002, Oxford University Press pp. 67, 113 and 117).*
Struijk et al. "Cuff Electrodes for Long-Term Recording of Natural Sensory Information, Studying the Relationship between Nerve Damage and Electrophysiological Parameters in Long-Term Implants" IEEE Engineering in Medicine and Biology vol. 28 p. 91-98, 1999.
Covington et al. "Simultaneous On-Line measuremetn of Blood K+, Ca2+, Na+, and pH with a Four-Function ChemFET Integrated-Circuit-Sensor" Clinical Chemistry vol. 30 p. 135-137, 1984.

(Continued)

*Primary Examiner* — Ernst V Arnold
(74) *Attorney, Agent, or Firm* — Brooks Kushman P.C.

(57) ABSTRACT

A method and apparatus for measuring activity in the peripheral nervous system comprises a nerve cuff having an array of chemical detectors such as chemFETS or ISFETS. Activity within the nerve causes chemical responses which can be detected. The use of chemical rather than electrical detection minimizes interference problems and allows the cuffs to be made smaller.

15 Claims, 2 Drawing Sheets

(56) References Cited

OTHER PUBLICATIONS

Bergveld "Thirty years of ISFETOLOGY What Happened in the past 30 Years and what may Happen in the next 30 Years" Sensors and Actuators B vol. 88, p. 1-20, 2003.

Bergveld et al. "How Electrical and Chemical Requirernents for Refet's may Coincide" Sensors and Actuators vol. 18, p. 309-327, 1989.

Wygladacz et al. "Design of Miniaturized Nitrite Sensors Based on Silicon Structure with Bacl-Side Contacts" Sensors and Actuators B vol. 83, p. 109-114, 2002.

Rozman et al. "Recording of ENGs from the Nerves Innervating the Pancreas of a Dog During the Intravenous Glucose Tolerance Test" Physiological Measurement vol. 23, p. 695-705, 2002.

Struijk et al. "Fascicle Selective Recording With a Nerve Cuff Electrode" IEEE Center for Sensory Motor Interaction p. 361-362.

* cited by examiner

METHOD AND APPARATUS FOR MEASURING ACTIVITY IN THE PERIPHERAL NERVOUS SYSTEM The present invention relates to a method and apparatus for measuring activity in the peripheral nervous system. The preferred interface is potentially fully-implantable, non-invasive to the nerve and could be eventually developed for chronic neural monitoring. One specific application relates to the use of a "cuff electrode"-type interface, placed around the Vagus nerve to detect activity in that nerve prior to and during a seizure. In such an application, the aim is to identify a specific pattern that predicts the onset of a seizure, and on the occurrence of that pattern to stimulate the Vagus nerve to prevent the seizure from occurring. On top of this rehabilitation scope, this platform could be used for diagnostic purposes in ambulatory patients.

Electrical stimulation of the Vagus nerve (Vagus Nerve Stimulation or VNS) has been reported as a method for treating epilepsy and more recently depression and is under investigation for treatment of Alzheimer's disease, anxiety and bulimia. VNS combined with normal use of anti-epilepsy drugs has been shown to reduce seizure frequency and to improve the condition of nearly 50% of patients, almost irrespective of age. Still, the application of the method is based on empirical studies, and it is uncertain exactly in what way VNS affects seizures and when it should be applied.

Typically, electrical stimulation of the Vagus nerve is carried out using the commercially available "helix-cuff" electrode, coupled to an implanted electrical stimulator that operates periodically with the option of manual operation in case the patient senses a seizure that hasn't been suppressed. Existing VNS schemes do suffer from a number of serious drawbacks. In particular, periodic stimulation is irrelevant to the possible occurrence of a seizure and power drain is high since the stimulator is operated continually. The device therefore requires battery change—and therefore surgery—every few years. Moreover, the interface used is unsophisticated, as it features no recording that would allow monitoring of seizure-related neural activity and no advanced stimulation techniques can be employed, as would be the case with a conventional tripolar cuff.

In addition to being used to stimulate nerves, cuff electrodes have also been used to measure and record activity within the peripheral nervous system. One example is described in Struijk J. J., Thomsen, M., Larsen, J. O. and Sinkjaer, T. "Cuff electrodes for long-term recording of natural sensory information" *IEEE Eng. Med. Biol.*, vol. 18, 91-98, 1999. Theoretically, the same cuff could be used for both recording and stimulation, although not simultaneously, as large stimulus currents will interfere with detection of the smaller neural electrical signals.

According to the present invention there is provided a nerve cuff having a plurality of chemical sensors for monitoring the activity of a nerve within the cuff.

According to a further aspect there is provided a method of measuring the activity of a nerve within the peripheral nervous system comprising surrounding the nerve with a cuff having a plurality of chemical sensors, and recording an output of each of the sensors. The sensors may be chemFETS or ISFETS.

The invention further extends to a method of in vivo treatment, comprising surrounding a nerve of the peripheral nervous system with a cuff having a plurality of chemical sensors, and stimulating the nerve in dependence upon outputs of the sensors.

One particular advantage of using chemFETS or ISFETS is that they may display different electrode-electrolyte interface characteristics resulting in different frequency responses and noise levels than metal electrodes. Electrode noise which tends to degrade conventional (electrical) recordings is likely to be a smaller obstacle when using chemFETS or ISFETS. ChemFETS often suffer from temperature drift; however, this is unlikely to be an issue inside the body, where temperature variation is minimal.

Preferably, the chemical sensors of the cuff are tuned to detect a variety of different ions, for example although not necessarily $K^+$, $Cl^-$ and $Na^+$. ChemFETs capable of measuring $K^+$ and $Na^+$ have been well established, as described in Sibbald A., Covington A. K. and Carter R. F. "Simultaneous on-line measurement of blood K+, Ca2+, Na+, and pH with a four-function ChemFET integrated-circuit sensor", Clinical Chem., vol. 30, 135-137, 1984, and similarly chemFETs for $Cl^-$ measurements have been described in Wygladacz K., Malinowska E., Jazwinski J. and Brzozka Z., "Design of miniaturized nitrite sensors based on silicon structure with back-side contacts", Sensors and Actuators B: Chem., vol. 83, 109-114, 2002.

The main advantage of using $K^+$ and $Na^+$ sensors in close proximity to the active nerve is that this provides a way of discriminating between neural activity and muscular interference, which degrades conventional neural recordings. Almost simultaneous variations in the concentrations of these two ions will occur only when the neural membrane "fires" an action potential. Such combined concentration change will not occur when muscle-triggered ionic currents flow through the cuff.

In addition to being used for recording purposes, embodiments of the invention may also provide electrical stimulation. By stimulating electrically while recording chemically so-called "stimulation artifacts" can largely be avoided.

Where the method and apparatus are used for rehabilitation/treatment purposes, it may be convenient to compare the real-time recorded results with previously collected data for the same patient. When a pattern of activity is detected which corresponds to a pattern which has in the past indicated the onset of (for example) a seizure, the system may be programmed automatically to stimulate the nerve.

BRIEF DESCRIPTION OF THE DRAWINGS

The invention may be carried into practice in a number of ways and one specific embodiment will now be described, by way of example, with reference to the accompanying drawings, in which:

In the preferred embodiment, the detection of activity within a nerve is achieved using a generally cylindrical cuff which is positioned, after brief surgery, around the nerve bundle to be studied. Once positioned, the cuff may be closed in any convenient way, for example as illustrated in any one of FIGS. 1(a), 2(c). FIG. 1(a) shows the slit along the tube, covered with a silicone flap; and FIG. 1(b) shows a so-called "spiral cuff" closure.

Figure 1:
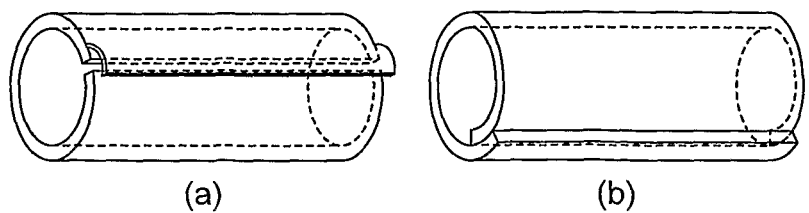
FIG. 1 shows a variety of closure arrangements for a nerve cuff in accordance with an embodiment of the present invention.
Figure 2:
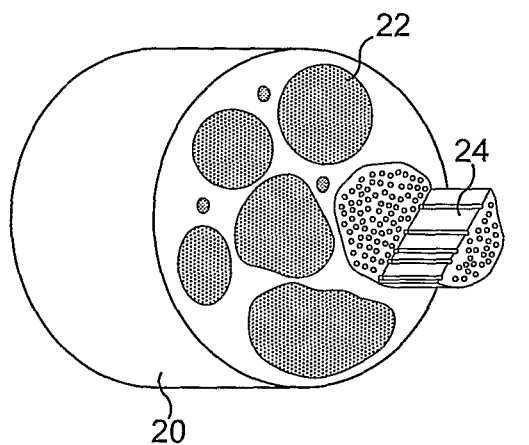
FIG. 2 shows a cross-section of a typical nerve bundle illustrating the way in which the nerve fibres are grouped into fascicles.
Figure 3:
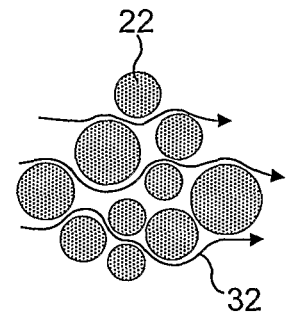
FIG. 3 gives an indication of possible paths of ionic currents flowing between fascicles.

A typical nerve bundle around which the cuff is to be located is shown in FIG. 2. The bundle 20 consists of several fascicles 22, each fascicle containing many individual nerve fibres 24. When an individual fibre or neuron fires, it exchanges ions with the surrounding extracellular space, through a mechanism called ion pumps. The firing of a group of nerves in one or more fascicles 22 creates ionic currents 32, as shown in FIG. 3, that flow between the fascicles to the extracellular space. As action potentials propagate along nerve fibres, ionic currents flow through the medium between the nerve bundle and the surrounding cuff, which can then be detected. The space restriction between the nerve bundle and the cuff increases the amplitude of the signal detected extraneurally. Thus, the local ionic flow that takes place during an action potential occurrence is concentrated inside the cuff.

Instead of detecting the electrical aspect of the signals, as in the prior art, the present embodiment makes use of chemical or ion detectors built into the cuff itself. One suitable detector is an ISFET (Ion Sensitive Field Effect Transistor), as described in Bergveld, P., "*Thirty years of ISFETOLOGY—what happened in the past 30 years and what may happen in the next 30 years*" Sens. Actuator B Chem. Vol. 88, pp. 1-20, 2003. This can be used to measure the ion concentration within a solution; when the ion concentration changes, the current flowing through the transistor changes accordingly. More generally, the detector may take the form of a chemFET (Chemical Field Effect Transistor). This is a type of field effect transistor that can be used to detect atoms, molecules and ions in liquids. It may be considered a structural analogue of a MOSFET transistor, where the charge on the gate electrode is proportional to the ionic concentration of the chemical species of interest.

Typically, the size of the sensors along the nerve axis will be such that at least one active node of Ranvier is under the sensor membrane.

The device may include three different species of chemFET or ISFET, respectively detecting changes in ionic concentrations of $Cl^-$, $Na^+$ and $K^+$. It is known that not all ions involved in neural conduction have equal intraneural and extraneural concentrations.

Thus, ionic flow created by EMG potentials through the cuff may involve mainly a certain type of ions (e.g. $Cl^-$), while an action potential occurrence would be associated with a rapid local concentration increase of $K^+$ immediately following $Na^+$ concentration decrease. Thus a combination of certain chemFET types could be used for detecting neural activity without being significantly affected by muscle interference.

Figure 4:
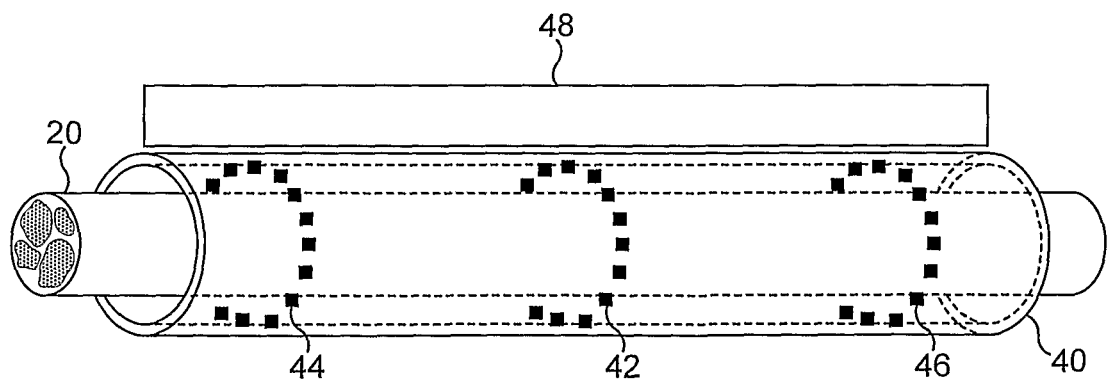
FIG. 4 shows a first proposed topology using three rings of detectors.

A typical cuff topology is shown schematically in FIG. 4. Within the body 40 of the cuff there are arrays of chemical electrodes forming three rings, 42, 44, 46, similar to the electrical tripolar cuff electrode counterpart. The electrodes are coupled to an attached circuit board 48 used for receiving and analysing the signals, as well as for data transmission to an external unit, which will also supply power wirelessly.

The operation and control of the device of FIG. 4, for recording purposes, may be similar to that used in a conventional tripolar recording cuff, as described for example in Struijk J. J., Haugland, M. K., and Thomsen, M. "*Fascicle Selective Recording with a Nerve Cuff Electrode*" 18th Annual International Conference of the IEEE Engineering in Medicine and Biology Society, Amsterdam, 1996 or in Rozman J., Zorko, B., Bunc, M., Mikac, U., and Tegou, E. "*Recording of ENGs from the nerves innervating the pancreas of a dog during the intravenous glucose tolerance test*" Physiological Measurement, vol. 23, 695-705, 2002.

The presence at least one of the end electrodes 40, 44, may assist in detecting the direction of the signal, making it possible to discriminate between sensory and motor signals when both take place within the nerve bundle.

Figure 5:
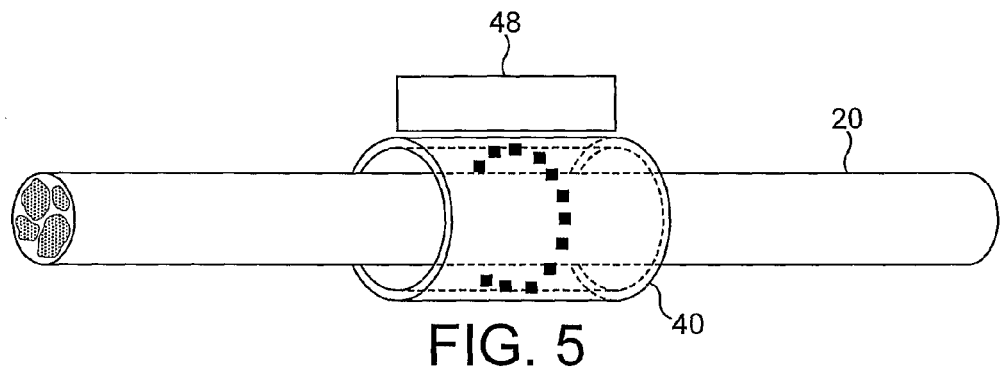
FIG. 5 shows a second topology using a single ring.

One particular advantage in using chemFETS or ISFETS instead of standard electrodes, is that cuff dimensions are not restricted by the same rules defined by theory that relates to signal amplitude and interference reduction. Accordingly, as shown in FIG. 5, it is possible to make a cuff of much smaller dimensions (e.g. 5 millimeters in length), covering just a few nodes of Ranvier. This makes the cuff very appropriate for implantation in more sites of interest, for example close to the spinal cord, intradurally, where the available space is limited.

Figure 6:
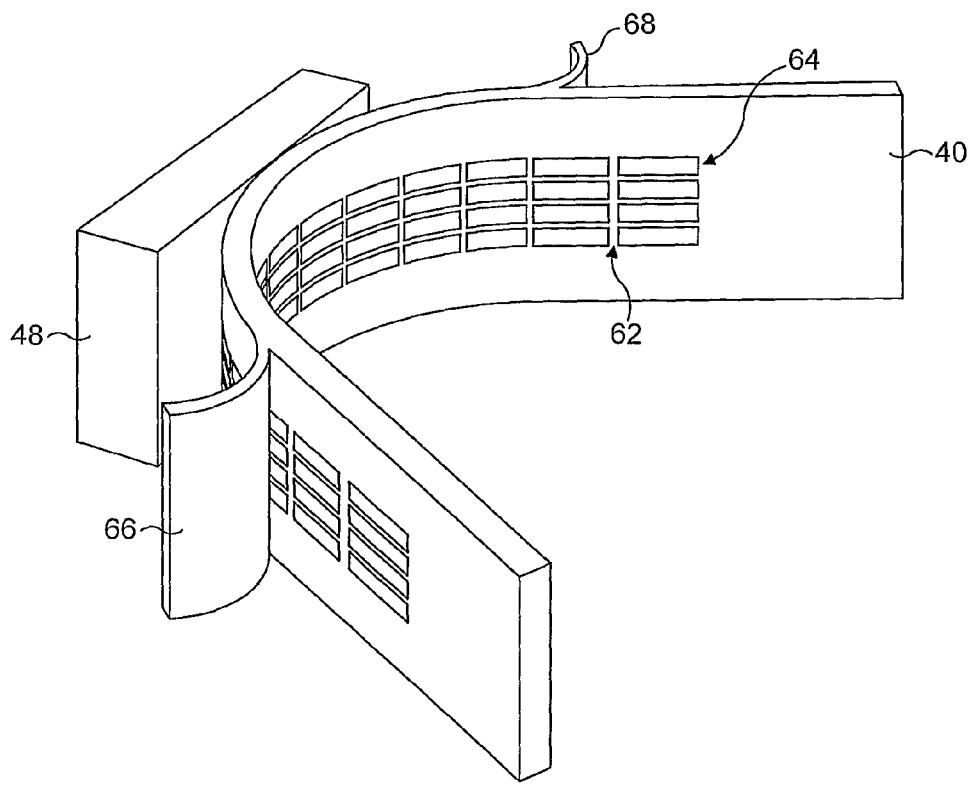
FIG. 6 shows the proposed cuff structure in more detail.

More details of a practical implementation of the device of FIG. 5 are shown in FIG. 6. In this example, the body 40 of the cuff is made of a flexible biocompatible plastic material such as silicone rubber or polyamide, with the detectors comprising a chemFET array 62. At one edge of the array 62 is a platinum reference electrode array 64. The elements of the chemFET arrays in FIG. 6 can be independent ICs placed on the inside wall of the cuff, with appropriate spacing so as to form multi-segment "rings" when the cuff assumes its cylindrical shape.

In order to make the chemFET interface biocompatible, DC signals should be avoided between the gate and the tissue. Thus instead of using a reference electrode as conventionally used in ISFETs a pseudo-reference electrode in combination with differential structures may be used. Details may be found in Bergvelt P., Van Der Berg, A., Van Der Wal, P. D., Skowronska-Ptasinska, M., Sudholter, E. J. R., and Reinhoudy, D. N. "How Electrical and Chemical Requirements for REFETs May Coincide" *Sensors and Actuators*, vol. 18, 309-327, 1989.

As an alternative to the pseudo-reference electrode, $K+$ and $Na+$ chemFETs can be used as reference chemFETs placed at the external wall of the cuff. These do not have to form an array, as one of each species will be adequate for acting as reference for the corresponding array located inside the cuff. Ion flows due to nerve activity will not be detectable in the middle of the outer wall of the cuff, thus the reference chemFETs will provide background ionic measurements. By use of multiplexing, each internal chemFET element will be combined in turn with its external counterpart, to form the input differential pair of a subsequent amplification stage, which will form the front-end circuitry of the neural sensing platform.

In order to restrain the device against angular displacement during acute experiments, externally extending flanges 66, 68 are provided.

The circuitry 48 is mounted to the cuff, and is contained within an encapsulated module. The electronics could either do all the necessary processing on chip or, alternatively, could simply collect the data and transmit it onwards for off-line analysis. Power supply and transmission of the data to an external processor could be via a wire (not shown) passing through the skin (in acute experiments) or via a wireless link.

Where appropriate, the cuff may be used in conjunction with a standard electrical stimulation cuff for providing stimulation to the nerve bundle, as required. Alternatively, the cuff may include its own stimulation electrodes (not shown). Similarly in addition to the chemFETS and/or ISFETS, the cuff may include conventional (electrical) recording electrodes.

Where the device includes means for stimulating as well as means for recording, the system may be configured automatically to stimulate the nerve on the measurement of a particular pattern of chemical activity. For the Vagus nerve, stimulation may be provided when the detected pattern of activity indicates that a seizure may be imminent. In this case, stimulation will not be used for activation of muscle groups or organs but rather for neuromodulation. This is a method of essentially stopping neural activity, thus blocking seizure-related motor signals when measurements indicate they are about to occur.

The invention claimed is:

1. A nerve cuff for monitoring neural electrical activity, comprising:
    a plurality of chemFET sensors provided on an inside wall of the nerve cuff and configured to monitor local changes in concentrations of a plurality of ionic species in proximity to neural tissue, wherein at least some of the plurality of sensors are sensitive to changes in concentration of $K^+$ ions and in which at least some of the plurality of sensors are sensitive to changes in concentration of ions other than $K^+$ ions;
    reference chemFET sensors provided on an external wall of the nerve cuff configured to provide background ionic measurements; and
    electronics configured to differentiate between neural signals and external interference signals using measured rapid local changes in concentration of K+ ions when compared with measured changes in concentration of the other ions.

2. A nerve cuff as claimed in claim 1 in which the sensors form a sensor array.

3. A nerve cuff as claimed in claim 2 further comprising a platinum reference array.

4. A nerve cuff as claimed in claim 2 in which the sensor array defines a ring.

5. A nerve cuff as claimed in claim 3 further comprising a central ring and first and second end rings.

6. A nerve cuff as claimed in claim 1 in which the sensors are of three types, respectively sensitive to $K^+$, $Cl^-$ and $Na^+$ ions.

7. A nerve cuff as claimed in claim 1 further comprising an electrical stimulation electrode, wherein the nerve cuff is configured to stimulate a nerve in response to a measurement of a pattern of chemical activity.

8. A nerve cuff as claimed in claim 1, further comprising electrodes for monitoring the electrical activity of a nerve within the cuff.

9. A nerve cuff as claimed in claim 1 further comprising a radially-extending flange for rotation-resistance.

10. A nerve cuff as claimed in claim 1, further comprising on-cuff electronics for recording or processing outputs from the sensors.

11. The nerve cuff of claim 1, wherein at least some of the plurality of sensors are sensitive to changes in concentration of $Na^+$ ions, and wherein the electronics are arranged to detect an occurrence of neural signals based on a rapid local concentration increase of $K^+$ ions immediately following a local concentration decrease of $Na^+$ ions.

12. The nerve cuff of claim 1 further comprising one or more electrodes arranged to detect the direction of the neural signal and discriminate between sensory and motor signals.

13. A method of measuring the activity of a nerve within the peripheral nervous system comprising:
    surrounding the nerve with a nerve cuff having a plurality of chemFET sensors provided on an inside wall of the nerve cuff and reference chemFET sensors provided on an external wall of the nerve cuff configured to provide background ionic measurements, and recording an output of each of the sensors;
    wherein at least some of the plurality of chemical sensors provided on the inside wall of the nerve cuff monitor changes in concentration of $K^+$ ions and at least some of the plurality of sensors monitor changes in concentration of ions other than $K^+$ ions, the method further comprising differentiating between neural signals and external interference signals using measured rapid local changes in concentration of $K^+$ ions when compared with measured changes in concentration of the other ions.

14. A method of treatment comprising:
    surrounding a nerve of the peripheral nervous system with a nerve cuff having a plurality of chemFET sensors provided on an inside wall of the nerve cuff and reference chemFET sensors provided on an external wall of the nerve cuff configured to provide background ionic measurements, and stimulating the nerve in dependence upon outputs of the sensors;
    wherein at least some of the plurality of chemical sensors provided on the inside wall of the nerve cuff monitor changes in concentration of $K^+$ ions and at least some of the plurality of sensors monitor changes in concentration of ions other than $K^+$ ions, the method further comprising differentiating between neural signals and external interference signals using measured rapid local changes in concentration of $K^+$ ions when compared with measured changes in concentration of the other ions.

15. A method of measuring neural electrical activity, comprising:
    surrounding a nerve of the peripheral nervous system with a nerve cuff having a plurality of chemFET sensors provided on an inside wall of the nerve cuff and reference chemFET sensors provided on an external wall of the nerve cuff configured to provide background ionic measurements;
    using the chemFET sensors to monitor changes in concentrations of one or more ionic species; and
    associating the monitored changes with electrical activity.

* * * * *